United States Patent
Pineau et al.

(10) Patent No.: US 8,217,164 B2
(45) Date of Patent: *Jul. 10, 2012

(54) USE OF A LACTOSE-DERIVED C-GLYCOSIDE COMPOUND AS AN AGENT FOR ACTIVATING AND REGULATING CUTANEOUS IMMUNITY

(75) Inventors: Nathalie Pineau, Herblay (FR); Maria Dalko, GIF S/Yvette (FR)

(73) Assignee: L'Oreal, Paris (FR)

( * ) Notice: Subject to any disclaimer, the term of this patent is extended or adjusted under 35 U.S.C. 154(b) by 638 days.

This patent is subject to a terminal disclaimer.

(21) Appl. No.: 12/296,304

(22) PCT Filed: Apr. 5, 2007

(86) PCT No.: PCT/EP2007/053364
§ 371 (c)(1),
(2), (4) Date: Dec. 11, 2008

(87) PCT Pub. No.: WO2007/116015
PCT Pub. Date: Oct. 18, 2007

(65) Prior Publication Data
US 2009/0275525 A1    Nov. 5, 2009

Related U.S. Application Data

(60) Provisional application No. 60/797,387, filed on May 4, 2006.

(30) Foreign Application Priority Data

Apr. 7, 2006  (FR) ..................... 06 51268

(51) Int. Cl.
| | | |
|---|---|---|
| *C07H 7/02* | (2006.01) | |
| *C07H 7/04* | (2006.01) | |
| *C13K 3/00* | (2006.01) | |
| *A61K 31/7016* | (2006.01) | |
| *A61K 31/7012* | (2006.01) | |
| *A61K 31/7028* | (2006.01) | |
| *A61K 31/7034* | (2006.01) | |

(52) U.S. Cl. ................................. 536/123.13
(58) Field of Classification Search ........................ None
See application file for complete search history.

(56) References Cited

U.S. PATENT DOCUMENTS

| | | | |
|---|---|---|---|
| 6,153,601 A | 11/2000 | Breton et al. | |
| 7,049,300 B2 * | 5/2006 | Dalko et al. | ............... 514/23 |
| 2004/0048785 A1 | 3/2004 | Dalko et al. | |
| 2006/0223763 A1 | 10/2006 | Dalko et al. | |
| 2010/0160251 A1 * | 6/2010 | Brenton | ................. 514/53 |

FOREIGN PATENT DOCUMENTS

| | | |
|---|---|---|
| EP | 0 818 201 | 1/1998 |
| WO | 02 051803 | 7/2002 |
| WO | 02 051828 | 7/2002 |
| WO | 03 105769 | 12/2003 |
| WO | 2006 090307 | 8/2006 |

OTHER PUBLICATIONS

Machine translation (Google Translate) of PCT publication WO02/051803 (Philippe etal.) Original published Jul. 4, 2002.*
U.S. Appl. No. 12/296,310, filed Oct. 7, 2008, Pineau, et al.
U.S. Appl. No. 12/296,304, filed Oct. 7, 2008, Pineau, et al.

* cited by examiner

*Primary Examiner* — Eric S Olson
(74) *Attorney, Agent, or Firm* — Oblon, Spivak, McClelland, Maier & Neustadt, L.L.P.

(57) ABSTRACT

The present invention relates to novel lactose-derived compounds of general formula (I) and to their use as agents for stimulating the immune system of the skin and/or as immunoregulators, and for preparing a composition containing a cosmetically or pharmaceutically acceptable medium, intended in particular to prevent and/or limit the appearance of cutaneous immune imbalances, in particular related to environmental stresses.

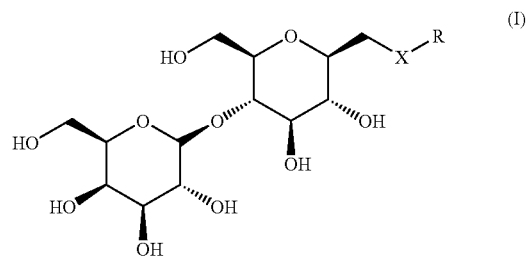

(I)

20 Claims, No Drawings

USE OF A LACTOSE-DERIVED C-GLYCOSIDE COMPOUND AS AN AGENT FOR ACTIVATING AND REGULATING CUTANEOUS IMMUNITY

CROSS-REFERENCE TO RELATED APPLICATIONS

The present application is a 35 U.S.C. §371 National Stage patent application of International patent application PCT/EP07/053,364, filed on Apr. 5, 2007, which claims priority to U.S. provisional patent application U.S. 60/797,387, filed on May 4, 2006, and French patent application FR 0651268, filed on Apr. 7, 2006, the contents of which are hereby incorporated by reference in their entirety.

The present invention relates to novel lactose-derived C-glycoside compounds and to their use as agents for stimulating the immune system of the skin and/or as immunoregulators, and for preparing a composition containing a cosmetically or pharmaceutically acceptable medium, intended in particular to prevent and/or limit the appearance of cutaneous immune imbalances, in particular related to environmental stresses.

Cutaneous immune disorders are normal physiological phenomena which appear with age. They can, however, be accelerated by infections with microorganisms (viruses and bacteria), stress, chronological ageing, ultraviolet rays, "urban" living conditions, etc.

The immune system comprises a collection of specialized cells which are subject to multiple control mechanisms that ensure their renewal, their activation and their differentiation, and are essential to a normal level of immunocompetence. The role of the immune system is to discriminate self from non-self in order to eliminate pathogenic agents and spontaneous tumours. Any cellular depletion, any incorrect immune regulation or any functional deficiency is liable to promote the occurrence of manifestations which range from discomfort to pathological disorders characterized by the disturbance of the mechanisms of recognition of self with respect to non-self, and a greater sensitivity with respect to microbial attacks and neoplastic processes.

The skin is an organ that is highly important for the organism and is recognized as one of the main active elements of the immune defense system. Three epidermal cell types participate in this system: keratinocytes, melanocytes and Langerhans cells. These cells, which are found only in the skin, play an essential role in the immune response, and in particular in antigen presentation.

Normal skin constitutes a barrier and is capable of defending itself against outside attacks, in particular chemical and mechanical attacks; in this respect, a certain number of defense reactions against environmental factors (climate, ultraviolet rays, tobacco, pollutants, etc.) and/or xenobiotic (such as, for example, certain medicaments) occur therein.

Various factors, such as atmospheric pollutants, detergents, allergens, UV radiation, etc., negatively affect, by virtue of their action on the skin, a variety of immune responses, both locally at the site of exposure, and systemically, at distant sites. This form of immunosuppression is in particular related to the induction of antigen-specific suppressor T cells. Impairment of the delayed response is particularly important since immune reactions generated by T lymphocytes are responsible for protection against many chronic infectious pathologies.

Pathologies also exist which are based not on an insufficiency of immune cells, but on an immune imbalance; this is the case, in particular, of atopic diseases and autoimmune diseases which present, respectively, an excess of Th-2 lymphocytes and an excess of Th-1 lymphocytes.

The prevalence of atopic diseases (accompanied by an excessive presence of Th-2-type lymphocytes, such as atopic dermatitis, gastrointestinal allergies, allergic rhinitis and conjunctivitis, asthma) and of autoimmune diseases (accompanied by an excessive presence of Th-1-type lymphocytes, such as psoriasis, vitiligo, diffuse scleroderma, lupus erythematosus, certain forms of alopecia, rheumatoid arthritis, type I diabetes) has gradually increased over the last few decades in western societies.

The explanation which has appeared to be the most plausible regarding the increase in Th-2-related conditions is the hygiene-related hypothesis which suggests that the rapid increase in atopic eczemas is related to the current cleanliness of environments and to the decrease in exposure to microorganisms at the beginning of life (Holt P G, in Nestlé Nutrition Workshop series Pediatric Program, Isolauri E et al ed, Allergic diseases and the environment, Karger A G, Basel, vol 53 pp 53-68, 2004).

During the allergic reaction, which can be explained by a reorientation of Th-1-type immune reactions towards Th-2-type responses, the interaction between the normal host and the allergen is altered. The allergic reaction is then accompanied by an imbalance in the immune response, which may then be induced by resident bacteria (Martinez F D, Respir Res: 2:129-132, 2001).

These atopic conditions are chronic and often systemic inflammatory reactions of complex origin (genetic and environmental factors). In these pathologies, the responses of type 2 (Th-2) T helper cells to "inoffensive" antigens (allergens) of the environment play a determining role in triggering allergic conditions (Romagnani S, Curr Opin Immunol 6:838-846, 1994). Th-2 cells explain the joint intervention, in the allergic inflammatory process, of B cells that produce E immunoglobulins (via the production of interleukins IL-4 and IL-13), and of mast cells (via the production of IL-5).

Moreover, it is also important to emphasize that, while there is currently an increase in allergic pathologies related to Th-2-type cells, at the same time, an increase in pathologies related to Th-1 cells (autoimmune diseases, such as type I diabetes, psoriasis or vitiligo) is observed in developing countries.

Th-1-type cells play an important role in the development of the delayed hypersensitivity reaction (DHR); thus, in certain chronic autoimmune diseases such as rheumatoid arthritis and thyroiditis, the skin lesions observed are of the DHR type, and the CD4 T cells within said lesions are mainly of the Th-1 type. Identical results have been obtained over the course of infectious diseases due to mycobacteria (tuberculosis, leprosy), over the course of Lyme disease and over the course of psoriasis.

Vitiligo is an acquired depigmentation disorder of the skin that affects 1% of the world's population, regardless of skin colour. Vitiligo is a skin disease in which the melanocytes (MCs) are eliminated from the basal layer of the epidermis in the lesions. This disappearance of melanocytes leads to a deficient pigmentation. In vitiligo lesions, the melanocytes are destroyed by MC-reactive T cells. The depigmentation frequently begins during adolescence.

For example, after an infection, UV radiation or a chemical/mechanical attack, the melanocytes are damaged. Under conditions of normal immune control, these impairments are controlled by the immune system which destroys the modified cells. In the case of vitiligo, these impairments are not correctly treated and they constitute a source of autoantibodies which will contribute to establishing the autoimmune pathology.

Thus, it appears that a therapy which would make it possible to reorient the Th-2 "allergic" or Th-1 "autoimmune" immune response towards a physiological balance would lead to products whose topical application could induce a regulation of local immune phenomena.

The applicant has now demonstrated that C-glycoside compounds of general formula (I) are capable both of stimulating the immune system of the skin and also of rectifying an immune imbalance between populations of Th-1 and Th-2 lymphocytes, and are capable of causing atopic or autoimmune disorders.

It is known that certain sugars such as aldoses, ketoses, deoxyoses or monosaccharide derivatives stimulate immune defenses (EP 0 818 201).

O-glycoside or C-glycoside molecules which modulate the immune system also exist, such as C-glycolipid compounds (WO 2003/105769), fucopeptides and amido-deoxygalactose derivatives (U.S. Pat. No. 5,962,660 and WO 96/29339).

According to a first subject thereof, the present invention relates to novel compounds of general formula (I):

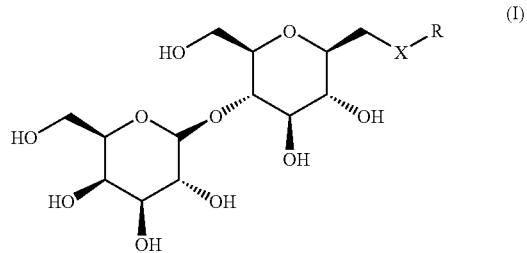

in which:
X represents a group chosen from: —CO—, —CH($NR_1R_2$)—, —CHR'— and —C(=CH R")—;
R represents a linear or branched, saturated or unsaturated alkyl, perfluoroalkyl or hydrofluoroalkyl chain, or a cycloalkyl, cycloperfluoroalkyl or cyclohydrofluoroalkyl ring, containing from 1 to 14 carbon atoms, or a phenyl radical, it being possible for said chain, said ring or said radical to be optionally interrupted with one or more heteroatoms chosen from oxygen, sulphur, nitrogen and silicon, and optionally substituted with at least one radical chosen from —OR'$_1$—, —SR"$_1$, —NR'"$_1$R'$_2$, —COOR"$_2$, —CONHR'"$_2$, —CN, halogen, perfluoroalkyl and hydrofluoroalkyl, and/or at least one cycloalkyl, aryl or heterocyclic radical, optionally substituted;
R', $R_1$ and $R_2$, which may be identical or different, have the same definition as R, and can also represent a hydrogen or a hydroxyl radical;
R" has the same definition as that given for R, and can also represent a hydroxyl radical;
R'$_2$ and R'"$_2$, which may be identical or different, represent a hydrogen atom, or a radical chosen from a hydroxyl radical and a linear or branched, saturated or unsaturated alkyl, perfluoroalkyl and/or hydrofluoroalkyl radical containing from 1 to 14 carbon atoms;
R'$_1$, R"$_1$, R"$_2$ and R'"$_1$, which may be identical or different, represent a hydrogen atom, or a radical chosen from a linear or branched, saturated or unsaturated alkyl, perfluoroalkyl and/or hydrofluoroalkyl radical containing from 1 to 14 carbon atoms;

with the following restrictions:
R1 and R2 cannot simultaneously be a hydroxyl radical;
R'2 and R'"1 cannot simultaneously be a hydroxyl radical;
if X is —CO—, then R cannot be a phenyl radical.

According to a second subject, the present invention relates to the use of compounds of general formula (I') encompassing general formula (I):

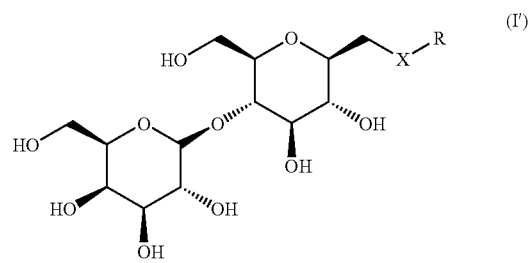

in which,
X represents a group chosen from: —CO—, —CH($NR_1R_2$)—, —CHR'— and —C(=CHR')—;
R represents a linear or branched, saturated or unsaturated alkyl, perfluoroalkyl or hydrofluoroalkyl chain, or a cycloalkyl, cycloperfluoroalkyl or cyclohydrofluoroalkyl ring, containing from 1 to 18 carbon atoms, or a phenyl radical, it being possible for said chain, said ring or said radical to be optionally interrupted with one or more heteroatoms chosen from oxygen, sulphur, nitrogen and silicon, and optionally substituted with at least one radical chosen from —OR'$_1$—, —SR"$_1$, —NR'"$_1$R'2, —COOR"$_2$, —CONHR'"$_2$, —CN, halogen, perfluoroalkyl and hydrofluoroalkyl, and/or at least one cycloalkyl, aryl or heterocyclic radical, optionally substituted;
R', $R_1$ and $R_2$, which may be identical or different, have the same definition as R, and can also represent a hydrogen and a hydroxyl radical;
R'$_2$ and R'"$_2$, which may be identical or different, represent a hydrogen atom, or a radical chosen from a hydroxyl radical and a linear or branched, saturated or unsaturated alkyl, perfluoroalkyl and/or hydrofluoroalkyl radical containing from 1 to 20 carbon atoms;
R'$_1$, R"$_1$, R"$_2$ and R'"$_1$, which may be identical or different, represent a hydrogen atom, or a radical chosen from a linear or branched, saturated or unsaturated alkyl, perfluoroalkyl and/or hydrofluoroalkyl radical containing from 1 to 20 carbon atoms;
with the following restrictions:
R1 and R2 cannot simultaneously be a hydroxyl radical;
R'2 and R'"1 cannot simultaneously be a hydroxyl radical;
for combating the weakening of the natural defenses of the skin which appears during chronological or photoinduced ageing and/or reinforcing the natural defenses of the skin.

Preference will be given to the compounds of general formulae (I) and (I') as defined above, such that:
R represents a linear or branched, saturated or unsaturated alkyl chain, or a cycloalkyl ring containing from 1 to 10 carbon atoms, or a phenyl radical, it being possible for said chain, said ring or said radical to be optionally substituted with at least radical chosen from —OR'$_1$—, —NR'"$_1$R'$_2$, —COOR"$_2$ and —CONHR'"$_2$;
R'$_2$ and R'"$_2$, which may be identical or different, represent a hydrogen atom, or a radical chosen from a hydroxyl radical and a linear or branched, saturated or unsaturated alkyl radical containing from 1 to 8 carbon atoms;

R'$_1$, R'''$_1$, R''$_2$ and R'''$_1$, which may be identical or different, represent a hydrogen atom, or a linear or branched, saturated or unsaturated alkyl radical containing from 1 to 8 carbon atoms.

More particularly, further preference will be given to the compounds of general formulae (I) and (I'), such that:

X represents a group chosen from: —CO—, —CH(NR$_1$R$_2$)— and —CHR';

R represents a linear or branched, saturated or unsaturated alkyl chain, or a cycloalkyl ring, containing from 1 to 10 carbon atoms, or a phenyl radical.

The C-glycoside compounds that can be used according to the invention represent a subfamily of the C-glycoside derivatives described in EP 1 345 919; they can be prepared according to the process described in said document.

Among the C-glycoside derivatives of formula (I) and/or (I') used according to the invention, the following are most particularly preferred:

Compound 1.
1-(C-β-D-Lactopyranosyl)propan-2-one;

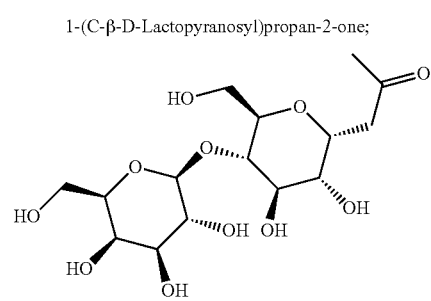

Compound 2.
1-(C-β-D-Lactopyranosyl)propan-2-one;

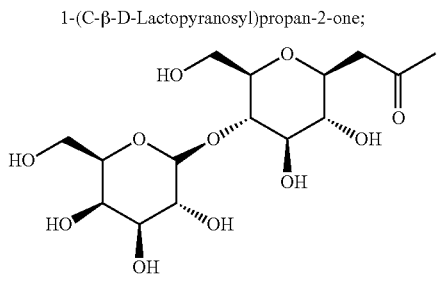

Compound 3.
1-(C-β-D-Lactopyranosyl)undecan-2-one;

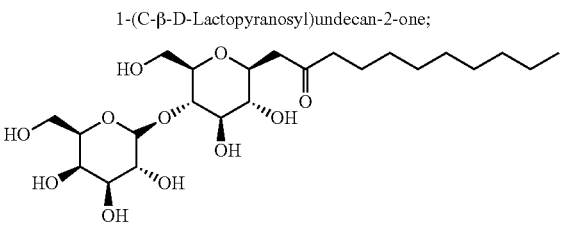

Compound 4.
1-(C-β-D-Lactopyranosyl)-2-hydroxypropane;

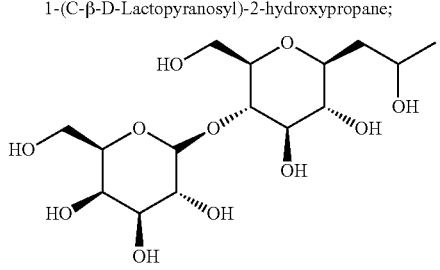

Compound 5.
1-[2-(3-Hydroxypropylamino)propyl]-C-β-D-lactopyranose;

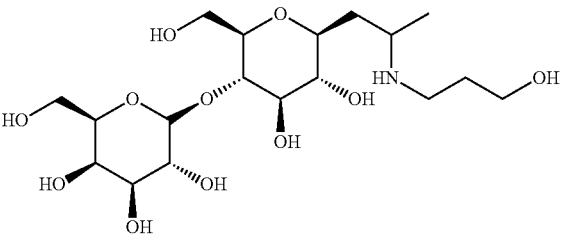

Compound 6.
Phenyl-2-(C-β-D-lactopyranosyl)-1-hydroxy-ethane

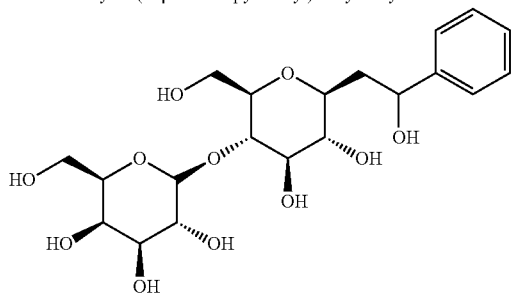

Compound 7.
3-Methyl-4-(C-β-D-lactopyranosyl)-2-butenoic acid ethyl ester;

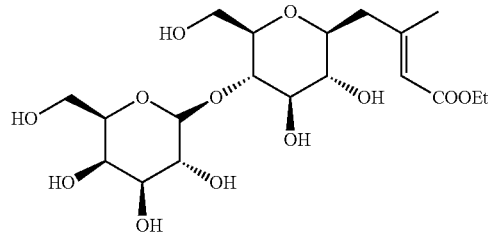

Compound 8.
3-Methyl-4-(β-D-lactopyranosyl)butyric acid ethyl ester.

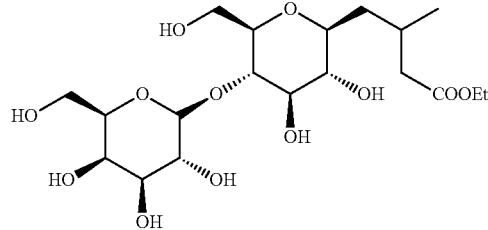

More particularly, the use of the C-glycosides of general formulae (I) and (I') according to the invention is suitable for preparing the skin against exposure to the sun.

Thus, the use according to the invention makes it possible to prevent and/or limit the harmful effects of exposure to UV rays.

The C-glycosides of general formulae (I) and (I') can also be used for maintaining a balance between Th-1 and Th-2 lymphocyte populations and/or for correcting an immune imbalance related to an excess of Th-1-type lymphocytes or Th-2-type lymphocytes.

These compounds according to the invention may therefore be advantageously used for combating undesirable manifestations of atopic type, in particular for treating reactive skin (characterized by red blotches, painful sensations, swelling), for preventing and/or decreasing itching, or else combating autoimmune conditions such as an imbalance in pigmentation of the skin and/or of the hair, in particular hair turning white or grey prematurely.

According to another of its subjects, the present invention relates to the use of C-glycoside compounds of general formulae (I) and (I'), for preparing a composition, comprising a physiologically acceptable medium, for use in the prevention and/or treatment of cutaneous autoimmune diseases or cutaneous atopic disorders.

More particularly, the cutaneous atopic disorders are chosen from cutaneous allergic reactions, atopic dermatitis and atopic eczema, and the cutaneous autoimmune diseases are chosen from delayed contact hypersensitivity, psoriasis, vitiligo, diffuse scleroderma, lupus erythematosus or certain forms of alopecia.

The term "immunostimulant agent" is intended to mean a compound whose administration to an organism results in the proliferation of the immune cells of said organism, for example the lymphocytes.

The term "immunoregulatory agent" is intended to mean an agent capable of maintaining and/or reestablishing a cutaneous immune balance between Th-1-type and Th-2-type cell populations, or else of correcting an excessive presence of Th-1-type or Th-2-type cells.

An immune imbalance may in particular be demonstrated by virtue of the increase, in an organism, of one or more cytokines characteristic of a lymphocyte type.

In fact, in addition to their classification according to the structure of their T receptor, Th-1-type and Th-2-type lymphocytes have been classified according to their cytokine protocol.

The cytokines characteristic of type 1 (Th-1) lymphocytes are IL-2, IFN-γ and TNF-β. The cytokines of type 2 (Th-2) lymphocytes are IL-4, IL-5, IL-9, IL-10 and IL-13.

More generally, the C-glycoside compounds of general formulae (I) and (I') can be used as an immunostimulant medicament in humans or in animals.

For this type of use, the compositions comprising the C-glycoside compounds of general formulae (I) and/or (I') can be administered, for example, parenterally, (intraperitoneally, subcutaneously, intramuscularly, intravenously, percutaneously), orally, nasally, conjuctivally, rectally or perlingually.

They can also be used by local application, for example by means of orally disintegrating tablets, in particular in non-specific immunotherapy of oral cavity diseases.

The medicament of the invention can be administered by way of prophylaxis, in the various cases above, and in particular for the prevention of recurring infections of the ear, nose and throat (ENT) sphere, and for the prevention of risks of infection in chronically ill patients.

The medicament of the invention is administered in particular as an immunostimulant treatment, in the ENT or bronchopulmonary field (rhinopharyngitis, laryngitis, sinusitis, sore throats, otitis, bronchitis, etc.) or in the dermatological field, in the case of bacterial, fungal or viral infections.

Preferably, the C-glycoside compound of general formulae (I) and (I') according to the invention will be formulated in a cosmetic or pharmaceutical composition intended to be applied topically to the skin, the scalp or the mucous membranes.

The compositions used according to the invention can be in any of the forms suitable for the applications envisaged, in particular topical application, in the cosmetics and dermatological fields.

The composition according to the invention contains a physiologically acceptable medium and one or more compounds according to the invention in an effective amount for stimulating the immunity of the skin or for reequilibrating the balance between Th-1 and Th-2 lymphocytes, for example in an amount ranging from 0.01% to 30% by weight, and preferably from 0.1% to 5% by weight, relative to the total weight of the composition.

The term "physiologically acceptable medium" is understood to mean a medium compatible with the skin and, optionally, with the mucous membranes, the nails, the scalp and/or the hair.

The composition according to the invention can be in the form in particular of an aqueous solution or a dispersion of the lotion or serum type, emulsions with a liquid or semi-liquid consistency, of the milk type, obtained by dispersion of a fatty phase in an aqueous phase (O/W) or vice versa (W/O), or suspensions or emulsions which are soft in consistency, of the aqueous or anhydrous gel or cream type, or else microcapsules or microparticles, or vesicular dispersions of ionic and/or non-ionic type. These compositions are prepared according to the usual methods.

This composition may be more or less fluid and may have the appearance of a white or coloured cream, an ointment, a milk, a lotion, a serum, a paste or a foam. It can optionally be applied to the skin in the form of an aerosol. It can also be in the form of a solid, for example in the form of a stick. It can be used as a care product, as a cleansing product, as a makeup product or alternatively as a shampoo or conditioner.

The composition according to the invention can be intended for a cosmetic or pharmaceutical, particularly dermatological, application. The composition according to the invention is preferably intended for a cosmetic application.

A subject of the invention is therefore also a cosmetic treatment process for the skin or for the scalp, comprising the topical application to the skin or the scalp of the composition described above.

Given the immunostimulant and equilibrating properties of the compounds according to the invention, this process is, in particular, intended to reinforce the natural defenses of the skin and to improve the cutaneous immune balance.

The C-glycoside compounds according to the invention will advantageously be combined with active agents for the hair, chosen from:
  anti-seborrhoeic agents, such as certain sulphur-containing amino acids, 13-cis-retinoic acid or cyproterone acetate;
  agents for combating squamous states of the scalp (dandruff), such as zinc pyrithione, selenium disulphide, climbazole, undecylenic acid, ketoconazole, piroctone olamine (octopirox) or cyclopiroctone (cyclopirox);
  active agents for stimulating hair regrowth and/or promoting the slowing down of hair loss; mention may more particularly be made, in a non-limiting manner, of:
  nicotinic acid esters, including in particular tocopheryl nicotinate, benzyl nicotinate and $C_1$-$C_6$ alkyl nicotinates, for instance methyl nicotinate or hexyl nicotinate;
  pyrimidine derivatives, such as 2,4-diamino-6-piperidinopyrimidine 3-oxide or "Minoxidil" described in U.S. Pat. No. 4,139,619 and U.S. Pat. No. 4,596,812; Aminexil or 2,4-diaminopyrimidine 3-oxide described in WO 96/09048;
  agents that are both lipoxygenase inhibitors and cyclooxygenase inducers, or cyclooxygenase-inducing agents that promote hair regrowth, such as those described by the applicant in European patent application EP 0 648 488;

antibiotics such as macrolides, pyranosides and tetracyclines, and in particular erythromycin;
cinnarizine, nimodipine and nifedipine;
hormones, such as estriol or the like, or thyroxine and salts thereof;
antiandrogenic agents, such as oxendolone, spironolactone, diethylstilbestrol and flutamide;
cromakalim and nicrorandil.

EXAMPLE 1

Demonstration of the Immunostimulant Activity of the C-Glycoside Derivatives of the Invention The immunostimulant activity is tested in the following way: human peripheral blood cells are cultured in the presence of an RPMI-type culture medium supplemented with L-glutamine (2 mM), penicillin/streptomycin (50 µg/50 IU/ml) and foetal calf serum (10%). The C-glycoside derivatives are added at various concentrations (10 to 0.05 mM), as is phytohaemagglutinin (PHA at 5*G/ml), a positive control for lymphocyte proliferation. After 3 days of culture, the proliferation is revealed by BrdU labelling.

The results obtained are as follows:

| Active agent | % stimulation relative to the control | | | | | |
|---|---|---|---|---|---|---|
| Concentrations (mM) | 10 | 5 | 1 | 0.5 | 0.1 | 0.05 |
| Compound 2: 1-(C-β-D-Lactopyranosyl)propan-2-one | 214 | 169 | 108 | 82 | 110 | 100 |

The derivative tested exhibits a strong capacity for human lymphocyte proliferation.

Compound 2 has a tendency to stimulate human lymphocyte proliferation at all the concentrations tested, this compound therefore has an immunostimulant activity.

EXAMPLE 2

Formulations

Face Care Gel

| | |
|---|---|
| Compound 1 | 0.05% |
| Thickening polymer | 1.00% |
| Antioxidant | 0.05% |
| Isopropanol | 40.00% |
| Preserving agent | 0.30% |
| Water | qs 100% |

Face Lotion for Hyperreactive Skin

| | |
|---|---|
| Compound 4 | 0.50 |
| Magnesium gluconate | 3.00 |
| Antioxidant | 0.05 |
| Isopropanol | 40.0 |
| Preserving agent | 0.30 |
| Water | qs 100% |

The invention claimed is:
1. A compound selected from the group consisting of:
1-[2-(3-hydroxypropylamino)propyl]-C-β-D-lactopyranose having the following structural formula:

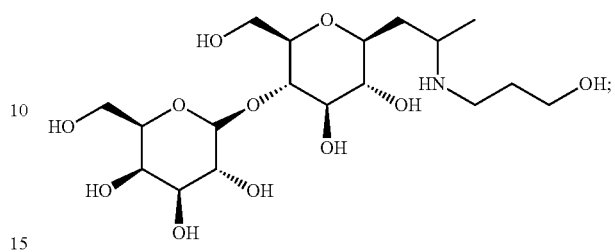

3-methyl-4-(C-β-D-lactopyranosyl)-2-butenoic acid ethyl ester having the following structural formula:

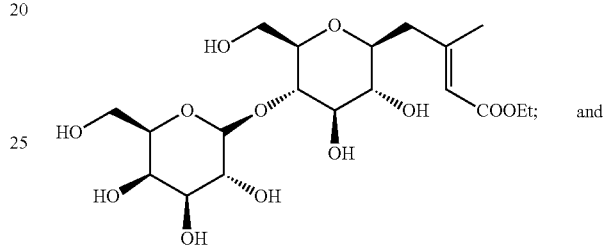

and 3-methyl-4-(β-D-lactopyranosyl)butyric acid ethyl ester having the following structural formula:

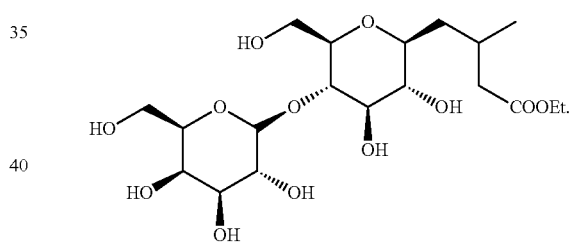

2. A composition comprising: one or more compounds according to claim 1; and a cosmetically, a physiologically or a pharmaceutically acceptable medium.

3. The composition according to claim 2, wherein the composition further comprises one or more active agents for hair.

4. A method for combating hair turning white or grey prematurely of a mammal having an immune imbalance comprising applying to the skin or the hair of the mammal a composition comprising: a cosmetically or physiologically acceptable medium; and one or more compounds according to the following general formula (I):

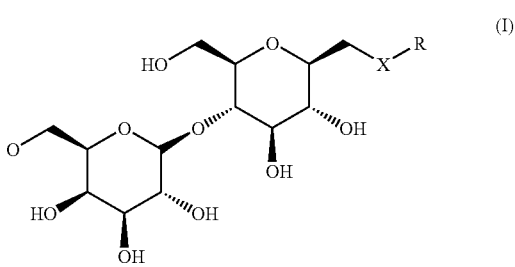

wherein:

X is selected from the group consisting of —CO—, —CH(NR$_1$R$_2$)—, —CHR'— and —C(=CHR")—;

R represents a linear or branched, saturated or unsaturated alkyl, perfluoroalkyl or hydrofluoroalkyl chain, or a cycloalkyl, cycloperfluoroalkyl or cyclohydrofluoroalkyl ring, comprising from 1 to 18 carbon atoms, or a phenyl radical, it being possible for said chain, said ring or said radical to be optionally interrupted with one or more heteroatoms selected from the group consisting of oxygen, sulphur, nitrogen and silicon, and optionally substituted with at least one radical selected from the group consisting of —OR'$_1$—, —SR"$_1$, —NR"'$_1$R'$_2$, COOR"$_2$, —CONHR"'$_2$, —CN, halogen, perfluoroalkyl and hydrofluoroalkyl, and/or at least one cycloalkyl, aryl or heterocyclic radical, optionally substituted;

R', R$_1$, and R$_2$, which may be identical or different, have the same definition as R, and can also represent a hydrogen and a hydroxyl radical;

R" has the same definition as that given for R, and can also represent a hydrogen and a hydroxyl radical;

R'$_2$ and R"'$_2$, which may be identical or different, represent a hydrogen atom, or a radical selected from the group consisting of a hydroxyl radical and a linear or branched, saturated or unsaturated alkyl, perfluoroalkyl and/or hydrofluoroalkyl radical comprising from 1 to 20 carbon atoms; and R'$_1$, R"$_1$, R"$_2$ and R"'$_1$, which may be identical or different, represent a hydrogen atom, or a radical selected from the group consisting of a linear or branched, saturated or unsaturated alkyl,
perfluoroalkyl and/or hydrofluoroalkyl radical comprising from 1 to 20 carbon atoms;
with the proviso that:
R$_1$ and R$_2$ cannot simultaneously be a hydroxyl radical; and
R'$_2$ and R"'$_1$ cannot simultaneously be a hydroxyl radical.

5. The method according to claim 4, wherein:
R represents a linear or branched, saturated or unsaturated alkyl, perfluoroalkyl or hydrofluoroalkyl chain, or a cycloalkyl, cycloperfluoroalkyl or cyclohydrofluoroalkyl ring, comprising from 1 to 14 carbon atoms, or a phenyl radical, it being possible for said chain, said ring or said radical to be optionally interrupted with one or more heteroatoms selected from the group consisting of oxygen, sulphur, nitrogen and silicon, and optionally substituted with at least one radical selected from the group consisting of —OR'$_1$—, —SR"$_1$, —NR"'$_1$R'$_2$, —COOR"$_2$, —CONHR"'$_2$, —CN, halogen, perfluoroalkyl and hydrofluoroalkyl, and/or at least one cycloalkyl, aryl or heterocyclic radical, optionally substituted;

R" has the same definition as that given for R, and can also represent a hydroxyl radical;

R'$_2$ and R"'$_2$, which may be identical or different, represent a hydrogen atom, or a radical selected from the group consisting of a hydroxyl radical and a linear or branched, saturated or unsaturated alkyl, perfluoroalkyl and/or hydrofluoroalkyl radical comprising from 1 to 14 carbon atoms; and R'$_1$, R"$_1$, R"$_2$ and R"'$_1$, which may be identical or different, represent a hydrogen atom, or a radical selected from the group consisting of a linear or branched, saturated or unsaturated alkyl, perfluoroalkyl and/or hydrofluoroalkyl radical comprising from 1 to 14 carbon atoms;
with the proviso that:
R$_1$ and R$_2$ cannot simultaneously be a hydroxyl radical;
R'$_2$ and R"'$_1$ cannot simultaneously be a hydroxyl radical; and
if X is —CO—, then R cannot be a phenyl radical.

6. The method according to claim 4, wherein:
R represents a linear or branched, saturated or unsaturated alkyl chain, or a cycloalkyl ring, comprising from 1 to 10 carbon atoms, or a phenyl radical, it being possible for said chain, said ring or said radical to be optionally substituted with at least one radical selected from the group consisting of —OR'$_1$, —NR"'$_1$R'$_2$, —COOR"$_2$ and —CONHR"'$_2$;

R'$_2$ and R"'$_2$, which may be identical or different, represent a hydrogen atom, or a radical selected from the group consisting of a hydroxyl radical and a linear or branched, saturated or unsaturated alkyl radical comprising from 1 to 8 carbon atoms; and R'$_1$, R"$_1$, R"$_2$ and R"'$_1$, which may be identical or different, represent a hydrogen atom, or a radical selected from the group consisting of a linear or branched, saturated or unsaturated alkyl radical comprising from 1 to 8 carbon atoms.

7. The method according to claim 4, wherein:
X is selected from the group consisting of —CO—, —CH(NR$_1$R$_2$)— and —CHR'; and
R represents a linear or branched, saturated or unsaturated alkyl chain, or a cycloalkyl ring, comprising from 1 to 10 carbon atoms, or a phenyl radical.

8. The method according to claim 4, wherein the one or more compounds according to the general formula (I) are selected from the group consisting of:

1-(C-β-D-lactopyranosyl)propan-2-one having the following structural formula:

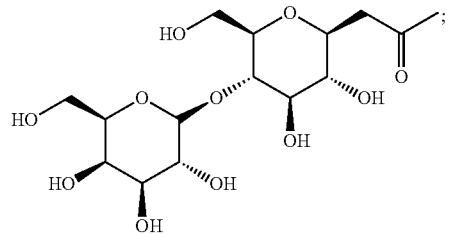

1-(C-β-D-lactopyranosyl)undecan-2-one having the following structural formula:

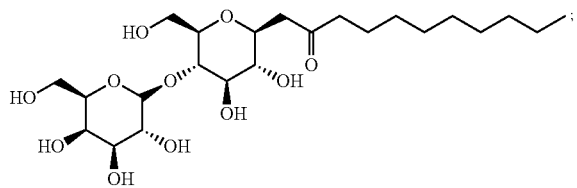

1-(C-β-D-lactopyranosyl)-2-hydroxypropane having the following structural formula:

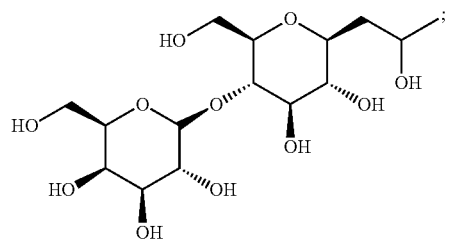

1-[2-(3-hydroxypropylamino)propyl]-CβO-D-lactopyranose having the following structural formula:

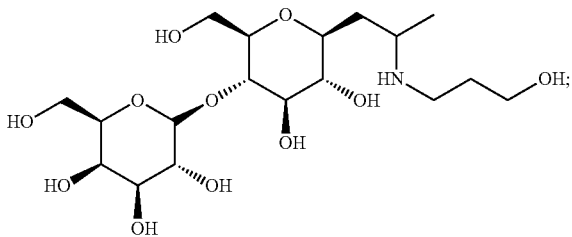

phenyl-2-(C-β-D-lactopyranosyl)-1-hydroxy-ethane having the following structural formula:

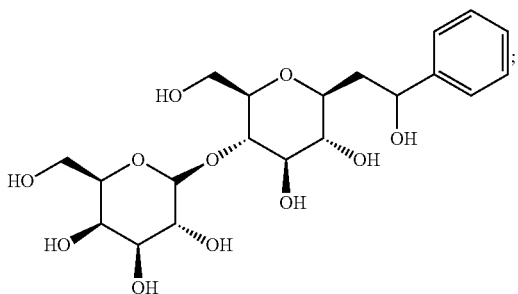

3-methyl-4-(C-β-D-lactopyranosyl)-2-butenoic acid ethyl ester having the following structural formula:

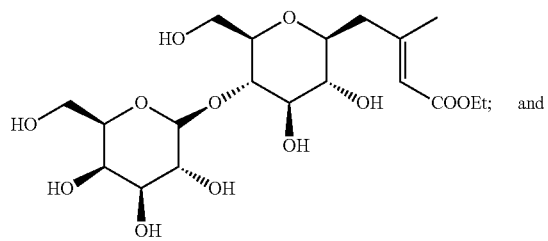

3-methyl-4-(β-D-lactopyranosyl)butyric acid ethyl ester having the following structural formula:

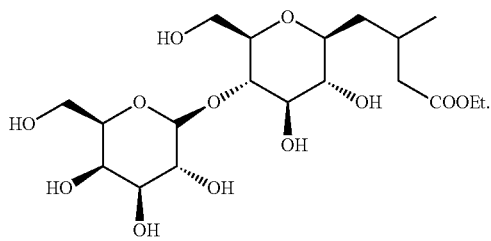

9. The method according to claim 4, wherein the composition further comprises one or more active agents for hair.

10. A method for treating a cutaneous autoimmune disease or a cutaneous atopic disorder of a mammal having an immune imbalance comprising administering to the mammal a composition comprising: a physiologically or pharmaceutically acceptable medium; and a therapeutically effective amount of one or more compounds selected from the group consisting of:

1-(C-β-D-lactopyranosyl)propan-2-one having the following structural formula:

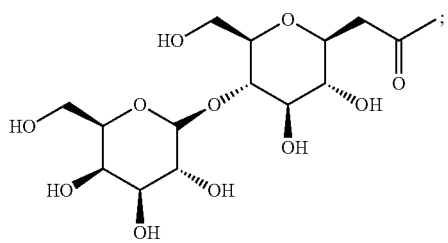

1-(C-β-D-lactopyranosyl)-2-hydroxypropane having the following structural formula:

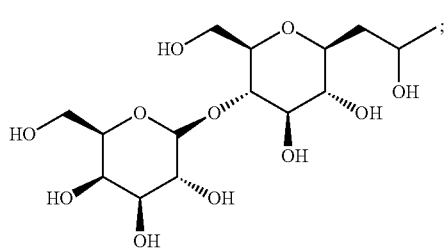

1-[2-(3-hydroxypropylamino)propyl]-C-β-D-lactopyranose having the following structural formula:

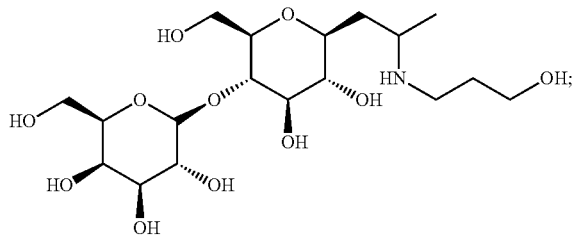

3-methyl-4-(C-β-D-lactopyranosyl)-2-butenoic acid ethyl ester having the following structural formula:

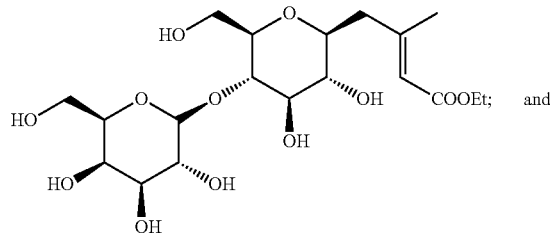

3-methyl-4-(β-D-lactopyranosyl)butyric acid ethyl ester having the following structural formula:

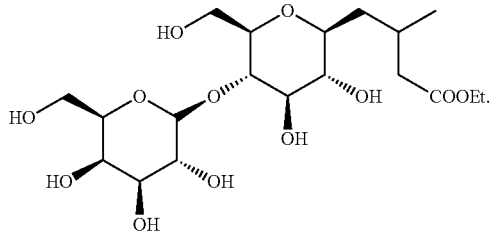

11. The method according to claim 10, wherein the method is for treating a cutaneous autoimmune disease selected from the group consisting of delayed contact hypersensitivity, psoriasis, vitiligo, diffuse scleroderma, lupus erythematosus and alopecia.

12. The method according to claim 10, wherein the method is for treating a cutaneous atopic disorder selected from the group consisting of cutaneous allergic reactions, atopic dermatitis and atopic eczema.

13. The method according to claim 10, wherein said administering comprises applying the composition to the skin, the scalp or the mucous membranes of the mammal.

14. The method according to claim 4, wherein the one or more compounds according to the general formula (I) are selected from the group consisting of:

1-(C-β-D-lactopyranosyl)propan-2-one having the following structural formula:

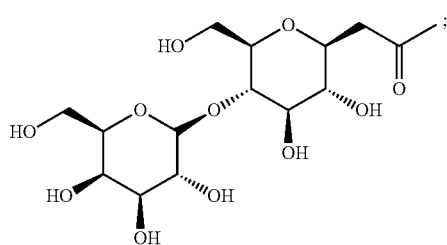

1-(C-β-D-lactopyranosyl)-2-hydroxypropane having the following structural formula:

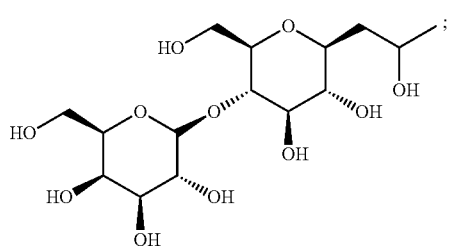

1-[2-(3-hydroxypropylamino)propyl]C-β-D-lactopyranose having the following structural formula:

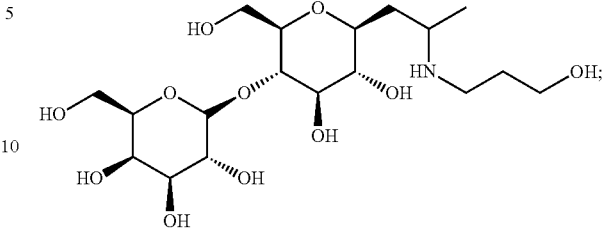

3-methyl-4-(C-β-D-lactopyranosyl)-2-butenoic acid ethyl ester having the following structural formula:

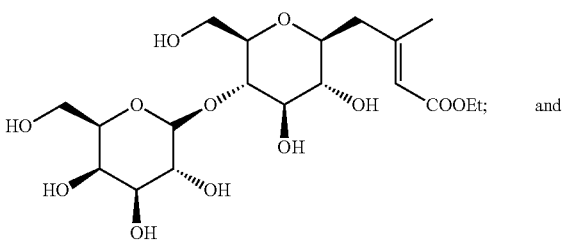 and 3-methyl-4-(β-D-lactopyranosyl)butyric acid ethyl ester having the following structural formula:

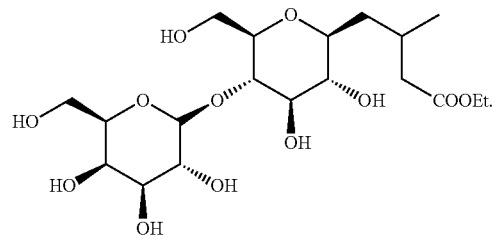

15. The method according to claim 4, wherein the compound according to the general formula (I) is 1-(C-β-D-lactopyranosyl)propan-2-one having the following structural formula:

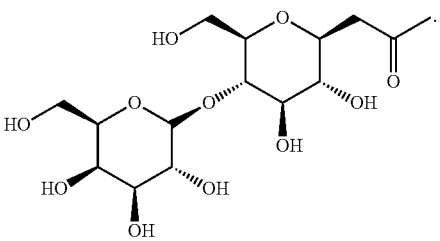

16. The method according to claim 4, wherein X is —CO—.

17. The method according to claim 10, wherein the compound according to the general formula (I) is 1-(C-β-D-lactopyranosyl)propan-2-one having the following structural formula:

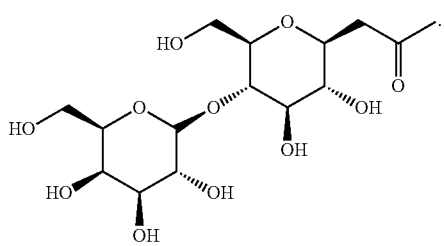

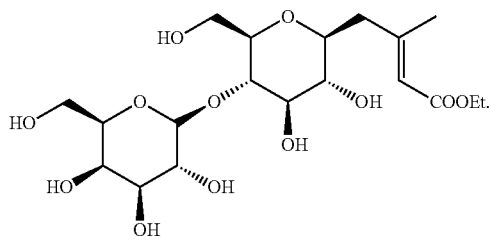

18. The compound according to claim 1, which is 1-[2-(3-hydroxypropylamino)propyl]-C-β-D-lactopyranose having the following structural formula:

20. The compound according to claim 1, which is 3-methyl-4-(β-D-lactopyranosyl)butyric acid ethyl ester having the following structural formula:

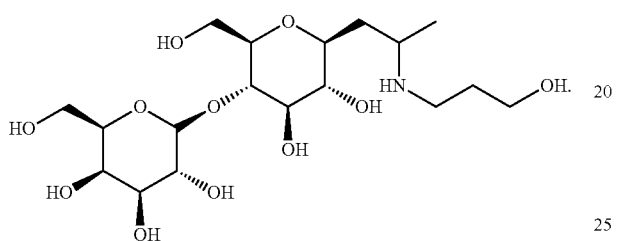

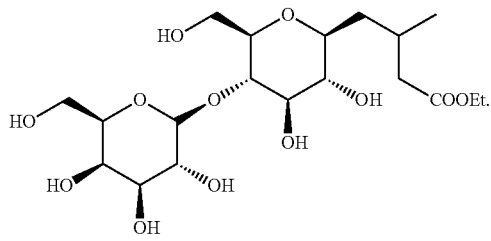

19. The compound according to claim 1, which is 3-methyl-4-(C-β-D-lactopyranosyl)-2-butenoic acid ethyl ester having the following structural formula:

* * * * *

UNITED STATES PATENT AND TRADEMARK OFFICE
CERTIFICATE OF CORRECTION

| | | |
|---|---|---|
| PATENT NO. | : 8,217,164 B2 | Page 1 of 1 |
| APPLICATION NO. | : 12/296304 | |
| DATED | : July 10, 2012 | |
| INVENTOR(S) | : Nathalie Pineau et al. | |

It is certified that error appears in the above-identified patent and that said Letters Patent is hereby corrected as shown below:

Column 11, line 45 "-SR'," should read -- -SR",--.

Signed and Sealed this
Eleventh Day of September, 2012

David J. Kappos
*Director of the United States Patent and Trademark Office*